(12) United States Patent  (10) Patent No.: US 8,337,522 B2
Ditter  (45) Date of Patent: Dec. 25, 2012

(54) VASCULAR SEALING DEVICE WITH LOCKING HUB

(75) Inventor: Theresa Ditter, Shoreview, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 1657 days.

(21) Appl. No.: 10/686,380

(22) Filed: Oct. 15, 2003

(65) Prior Publication Data
US 2005/0085852 A1  Apr. 21, 2005

(51) Int. Cl.
A61D 1/00 (2006.01)

(52) U.S. Cl. .................................. 606/213

(58) Field of Classification Search ........... 623/23.72; 606/213, 215–218
See application file for complete search history.

(56) References Cited

U.S. PATENT DOCUMENTS

| 4,135,272 A * | 1/1979 | Stephenson | 15/147.1 |
|---|---|---|---|
| 4,458,385 A * | 7/1984 | Espinoza | 24/16 PB |
| 5,662,681 A | 9/1997 | Nash et al. | 606/213 |
| 5,700,277 A | 12/1997 | Nash et al. | 606/213 |
| 5,728,114 A | 3/1998 | Evans et al. | 606/148 |
| 5,810,884 A | 9/1998 | Kim | 606/213 |
| 5,830,130 A | 11/1998 | Janzen et al. | 606/213 |
| 5,861,004 A | 1/1999 | Kensey et al. | 606/213 |
| 5,935,147 A | 8/1999 | Kensey et al. | 606/213 |
| 6,045,569 A | 4/2000 | Kensey | 606/213 |
| 6,086,607 A | 7/2000 | Cragg et al. | 606/213 |
| 6,090,130 A | 7/2000 | Nash et al. | 606/213 |
| 6,132,439 A | 10/2000 | Kontos | 606/139 |
| 6,179,863 B1 | 1/2001 | Kensey et al. | 606/215 |
| 6,197,042 B1 | 3/2001 | Ginn et al. | 606/213 |
| 6,535,764 B2 * | 3/2003 | Imran et al. | 607/40 |
| 6,896,692 B2 * | 5/2005 | Ginn et al. | 606/213 |
| 2002/0183787 A1 * | 12/2002 | Wahr et al. | 606/213 |
| 2003/0176890 A1 * | 9/2003 | Buckman et al. | 606/213 |

* cited by examiner

Primary Examiner — Gary Jackson
Assistant Examiner — Eric Blatt
(74) Attorney, Agent, or Firm — Holland & Hart LLP

(57) ABSTRACT

An internal tissue puncture closure method and apparatus. The method and apparatus provide a locking device for compressing and holding an external component such as a collagen sponge at a puncture situs. The locking device facilitates compression of the external component in a first direction, but prevents or locks against retraction.

34 Claims, 5 Drawing Sheets

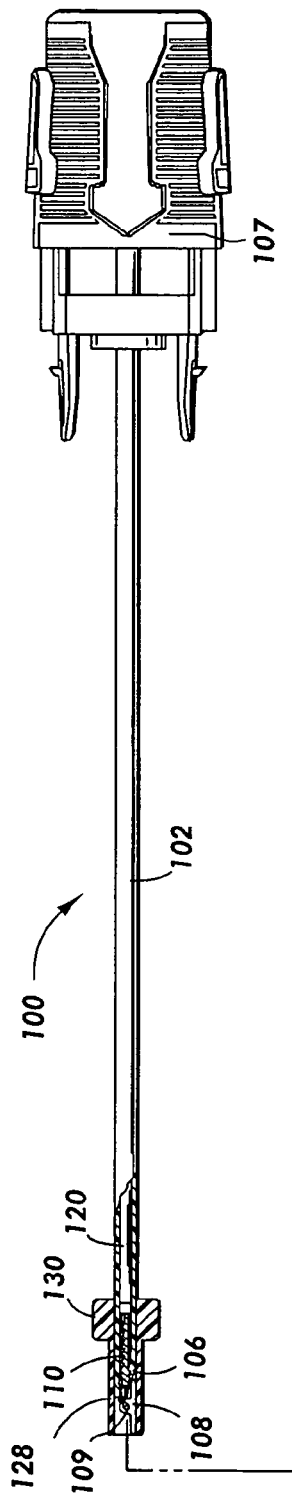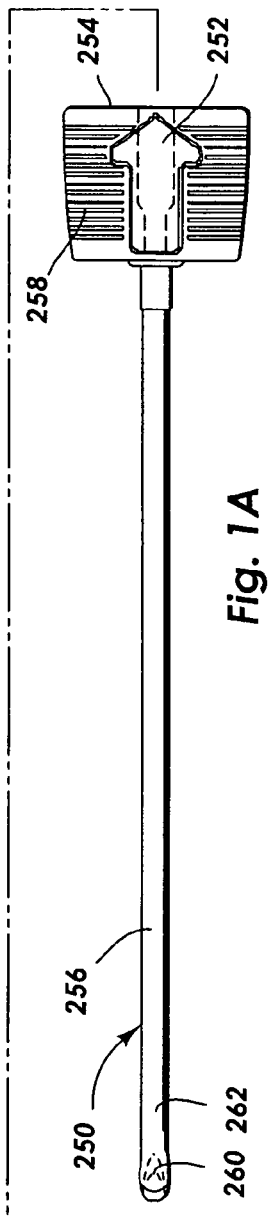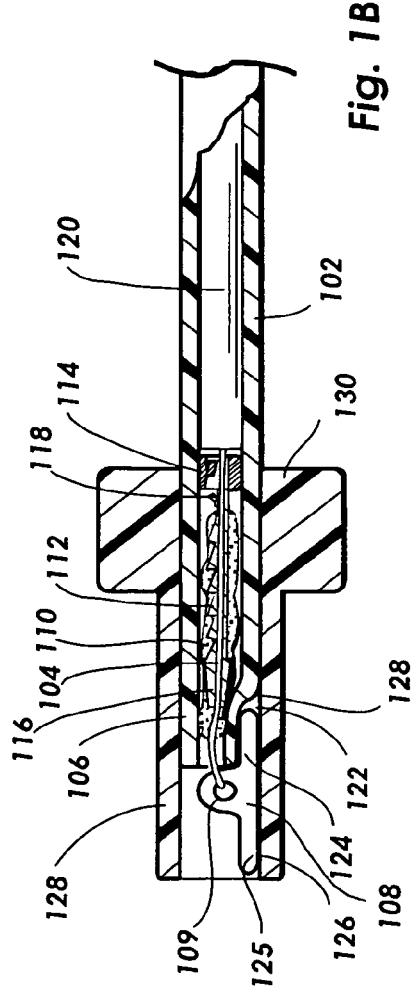
Fig. 1A
Fig. 1B

VASCULAR SEALING DEVICE WITH LOCKING HUB

FIELD OF THE INVENTION

The present invention relates to medical devices, and, more particularly, to an internal tissue puncture closure apparatus.

BACKGROUND OF THE INVENTION

Various medical procedures, particularly cardiology procedures, involve accessing a corporeal vessel or other lumen through a percutaneous sheath. The access to the vessel necessarily requires the formation of a hole or puncture in the vessel wall so that a medical procedure can be performed. After the particular medical procedure has been performed, the sheath and other tools must eventually be removed from the vessel and the access hole in the vessel wall must be closed.

A number of prior vascular closure devices have been developed to close the hole in the vessel wall. Closing the hole in the vessel wall typically involves packing a resorbable sealing plug at the hole or sandwiching the hole between the sealing plug and an anchor. Examples of prior vascular closure devices are described in U.S. Pat. Nos. 6,179,863; 6,090,130; and 6,045,569 and related patents that are hereby incorporated by reference.

However, prior to a successful deployment of the sealing plug or another vascular tool, the insertion sheath must be properly located within the vessel or other lumen. Proper placement of the insertion sheath enables proper placement of the sealing plug or insertion of a vascular tool.

According to conventional techniques, proper placement of the insertion sheath is accomplished with the aid of a puncture locator. Typically, the puncture locator and the insertion sheath are inserted partially through the hole in the vessel wall. The puncture locator includes a fluid communication path between distal (where the puncture locator enters the vessel) and proximal ends thereof, such that blood flow can be observed by an operator when the distal end enters the vessel. As the sheath penetrates the vessel wall, blood flows through the fluid communication path and out of a drip hole. Blood continues to flow through the puncture locator until the sheath and/or puncture locator are removed from the vessel. Usually the orientation between the puncture locator and the insertion sheath can be fixed, such that locating the puncture with the puncture locator also properly places the insertion sheath.

Usually the sealing plug is placed at the hole via a sealing device that is inserted through the properly placed insertion sheath. The sealing plug is packed at the hole by manually tamping the sealing plug toward the hole with a tamping tube. The sealing plug most often provides a sufficient seal of the hole as a result of the tamping. However, the sealing plug tends to expand, move, or reposition itself following the tamping operation. Sometimes the repositioning of the sealing plug compromises the seal, and bleeding occurs. In addition, sometimes the sealing plug is over-tamped, pushing a portion of the plug into the vessel which may result in complications. Therefore, there is a need for an improved vascular sealing device that prevents over-tamping and repositioning of the sealing plug to more effectively seal the hole.

SUMMARY OF THE INVENTION

In one of many possible embodiments, the present invention provides a tissue puncture closure device for partial insertion into and sealing of an internal tissue wall puncture. The tissue puncture closure device comprises a filament, an anchor for insertion through the tissue wall puncture attached to the filament at a first end of the closure device, a sealing plug disposed proximal of the anchor, and a locking apparatus arranged adjacent to the sealing plug for compressing the sealing plug toward the anchor. According to some embodiments the locking apparatus is a strap and hub attached to the filament. The strap and hub comprise a ratchet such that the hub may advance in a first direction, but may not retract opposite of the first direction. Therefore, to create the ratchet the strap may include an elongated track and a plurality of sloping teeth, and the hub may include a nut with a flexible internal finger biased to engage the plurality of sloping teeth. The flexible internal finger may traverse the teeth in the first direction, but the teeth prevent movement of the hub in a second direction opposite of the first direction. The strap may also include a shoulder stop limiting movement of the hub in the first direction. The device may include a tube slidingly disposed about the filament proximal to the hub for advancing the hub along the strap.

Another embodiment provides a tissue puncture sealing device comprising an internal component configured to be positioned against an internal wall of a lumen, an external component configured to be positioned external to the lumen, such that the external component is operatively connected to the internal component by a locking apparatus, and where the locking apparatus is configured to compress and hold the internal and external components together. According to some embodiments the internal component is an anchor and the external component is a collagen sponge. Likewise, the locking apparatus may comprise a strap and hub as mentioned above.

The invention also provides a method of sealing a puncture in an internal tissue wall accessible through a percutaneous incision including inserting a closure device at least partially into the percutaneous incision, advancing a one-way hub along a strap, and compressing a sealing plug toward the puncture by the advancing of the one-way hub along the strap.

The foregoing and other features, utilities and advantages of the invention will be apparent from the following more particular description of preferred embodiments of the invention as illustrated in the accompanying drawings.

BRIEF DESCRIPTION OF THE DRAWING

The accompanying drawings illustrate various embodiments of the present invention and are a part of the specification. The illustrated embodiments are merely examples of the present invention and do not limit the scope of the invention.

FIG. 1A is a cutaway assembly view of an internal tissue puncture closure device and an insertion sheath according to one embodiment of the present invention.

FIG. 1B is a detail of the cutaway portion of the internal tissue puncture closure device of FIG. 1A.

Throughout the drawings, identical reference numbers designate similar, but not necessarily identical, elements.

DETAILED DESCRIPTION

Figure 2:
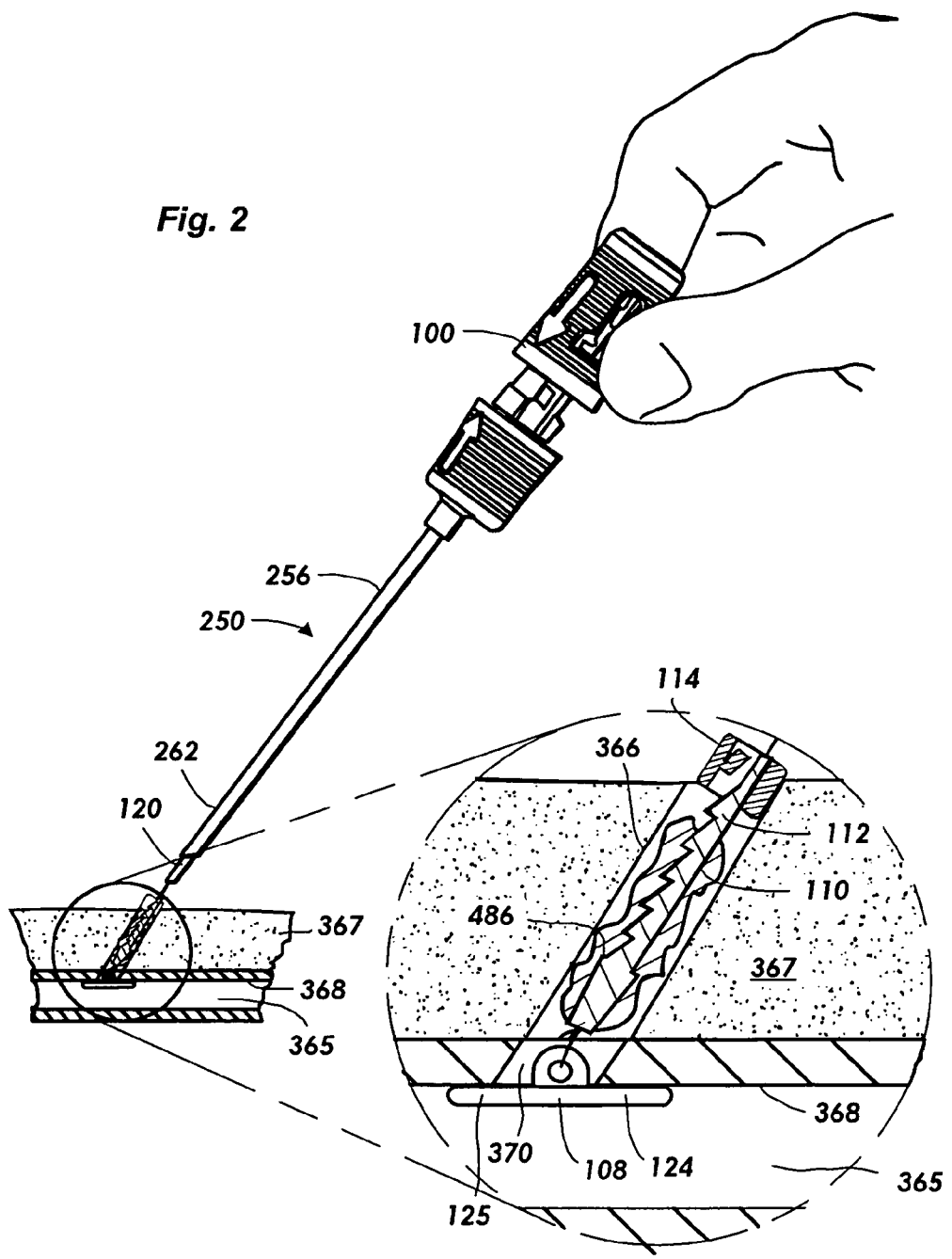
FIG. 2 is a perspective view of the tissue puncture closure device engaged with the insertion sheath and partially inserted into an internal tissue wall puncture according to one embodiment of the present invention.

The present specification describes techniques and apparatus for closing an internal tissue wall puncture, preferably using a closure device and an insertion sheath, while reducing the effects of over-tamping and sealing plug repositioning. While the methods and devices shown and described below include insertion sheaths and puncture sealing devices, the application of a locking apparatus to the secure a sealing plug is not limited to these specific devices. The principles described herein may be used to deploy and retain any sealing plug, particularly sealing plugs used to close punctures or incisions in bodily lumens. Therefore, while the description below is directed primarily to arterial procedures, the methods and apparatus may be used according to principles described herein with any lumen to control bleeding.

As used in this specification and the appended claims, the term "tissue" means an aggregation of morphologically similar cells and associated intercellular matter acting together to perform one or more specific functions in a body. "Ratchet" is used broadly to describe any mechanism that allows movement of a component by degrees in one direction only. A "lumen" is any open space or cavity in a bodily organ, especially in a blood vessel. The term "track" refers to a path or course along which something moves.

Referring now to the drawings, and in particular to FIGS. 1A-1B, an internal tissue wall puncture closure assembly including a tissue puncture closure device 100 and an insertion sheath 250 is shown according to one embodiment of the present invention. The tissue puncture closure device 100 includes a carrier tube 102 with a filament such as a suture 104 extending at least partially therethrough. According to FIGS. 1A-1B, the suture 104 extends from a first or distal end 106 of the closure device 100 to a second or proximal end 107 of the closure device 100. External to the first or distal end 106 of the carrier tube 102 is an internal component, which according the present embodiment is an anchor 108. The anchor is an elongated, stiff, low-profile member with a protruding eye 109. The anchor 108 is made of a non-hemostatic biologically resorbable polymer.

The suture 104 is also made of a biologically resorbable material and is threaded through the anchor 108. An external component, which, according to the present embodiment, is a biologically resorbable collagen sponge 110 that acts as a sealing plug, is initially disposed within the carrier tube 102 proximal of the anchor 108. The collagen sponge 110 is slidingly arranged adjacent to a locking apparatus for compressing the collagen sponge 110 toward the anchor 108. According to FIGS. 1A-1B, the collagen sponge 110 is freely arranged about the locking apparatus.

The locking apparatus of FIGS. 1A-1B comprises a strap 112 and a hub 114. However, other components in addition to or alternative to the strap 112 and the hub 114 may also be used as a locking apparatus. The locking apparatus may include any mechanism that compresses the collagen sponge 110 and holds or locks it in a desired position. While the locking apparatus may embody multiple forms, one particular embodiment including the strap 112 and the hub 114 is described and illustrated in detail below.

According to the present embodiment, the strap 112 of the locking apparatus is attached to the suture 104, and the hub 114 is movably arranged about the strap 112. Therefore, the hub 114 is indirectly attached to the suture 104. The strap 112 may be molded around the suture 104 to form an integral unit as shown, such that the suture 104 extends from both first and second ends 116, 118 of the strap 112. Alternatively, the strap 112 may include a hole through which the suture 104 may extend to fasten the strap 112 to the suture 104. It will be understood by those of skill in the art having the benefit of this disclosure, however, that other fasteners between the suture 104 and the strap 112 may also be used.

FIG. 2 shows the suture 104 extending distally from the strap 112 so that the locking apparatus terminates proximal of a distal end of the suture 104. The suture 104 provides a pivotal connection between the anchor 108 and the strap 112 as shown in a comparison between FIGS. 1B and 2.

The collagen sponge 110 is disposed around the strap 112 distal to the hub 114. The fit of the collagen sponge 110 around the strap 112 is preferably snug such that the collagen sponge 110 tends to remain in place until acted upon by a deliberate force. Therefore, while the collagen sponge 110 is snugly arranged about the strap 112, a force from the hub 114 on the collagen sponge 110 will cause it to slide over the strap 112 as discussed in more detail below.

The tissue puncture closure device 100 also includes a tamping tube 120 disposed within the carrier tube 102 proximal to the collagen sponge 110 and the hub 114. The tamping tube 120 is slidingly mounted over the suture 104. The tamping tube 120 has an outer diameter that is larger than an inner diameter of the hub 114 so that an operator may apply a force to the tamping tube 120 and advance the hub 114 distally along the strap 112. Advancing the hub 114 along the strap compresses the collagen sponge 110 and causes it to slide toward the anchor 108 to plug a percutaneous tissue puncture (See FIGS. 2-3).

At the distal end 106 of the carrier tube 102 is a nest 122. Prior to deployment of the anchor 108 within an artery, the protruding eye 109 seats outside the distal end 106 of the carrier tube 102, and one wing 124 of the anchor 108 rests in the nest 122. The nest 122 is typically crushed into the carrier tube 102 to a sufficient depth such that a surface 126 of the anchor 108 is flush with an outer diameter of the carrier tube 102. The nest 122 is crushed to a length that is longer than the wing 124 of the anchor 108. The anchor 108 may be temporarily held in place in the nest 122 by a bypass tube 128 disposed over the distal end 106 of the carrier tube 102.

The flush arrangement of the anchor 108 and carrier tube 102 allows the anchor 108 to be inserted into the insertion sheath 250, and eventually through an internal tissue puncture. However, the bypass tube 128 includes an oversized head 130 that prevents the bypass tube 128 from passing through an internal passage 252 of the insertion sheath 250. Therefore, as the puncture closure device 100 is inserted into the internal passage 252 of the insertion sheath 250, the oversized head 130 bears against a surface 254 of the insertion sheath 250. Further insertion of the puncture closure device 100 results in sliding movement between the carrier tube 102 and the bypass tube 128, releasing the anchor 108 from the bypass tube 128. However, the anchor 108 remains in the nest 122 following release from the bypass tube 128, limited in movement by the internal diameter of the carrier tube 102.

The insertion sheath 250 comprises a generally flexible tubular member 256 with a hemostatic valve 258 at a proximal end thereof. The insertion sheath 250 includes a fold 260 disposed at a first or distal end 262 thereof. The fold 260 acts as a one-way valve to the anchor 108. The fold 260 is a plastic deformation in a portion of the tubular member 256 that elastically flexes as the anchor 108 is pushed out through the first end 262 of the tubular member 256. However, as the anchor 108 passes though and out of the first end 262 of the tubular member 256, the fold 260 attempts to spring back to its original deformed position such that the fold 260 engages the carrier tube 102.

Referring next to FIG. 2, after the anchor 108 passes through the first end 262 of the tubular member 256, the anchor 108 enters a puncture 370 in an artery 365 or other lumen through a percutaneous incision 366 in a patient 367. The puncture 370 in the artery 365 is commonly referred to as an arteriotomy. When the anchor 108 enters the artery 365, it rotates and deploys such that its wings 124, 125 are arranged adjacent to an internal wall 368 of the artery 365. The puncture closure device 100 may be pulled in a proximal direction with respect to the insertion sheath 250 to facilitate rotation of the anchor 108 to the position shown. The fold 260 (FIG. 1A) in the insertion sheath 250 prevents reinsertion of the anchor 108 into the insertion sheath 250 and causes the anchor 108 to rotate if it does not do so automatically after passing out of the insertion sheath 250.

When the anchor 108 is properly positioned inside the artery 365 with its wings 124, 125 abutting the internal wall 368, the closure device 100 and the insertion sheath 250 are withdrawn from the percutaneous incision 366 together. However, because the anchor 108 is established inside the artery 365, retraction of the insertion sheath 250 and the closure device 100 exposes the collagen sponge 110, the strap 112 and hub 114, and the tamping tube 120. Accordingly, the collagen sponge 110 is deposited at an external situs of the puncture 370 in the artery 365 opposite of the anchor 108.

Figure 3:
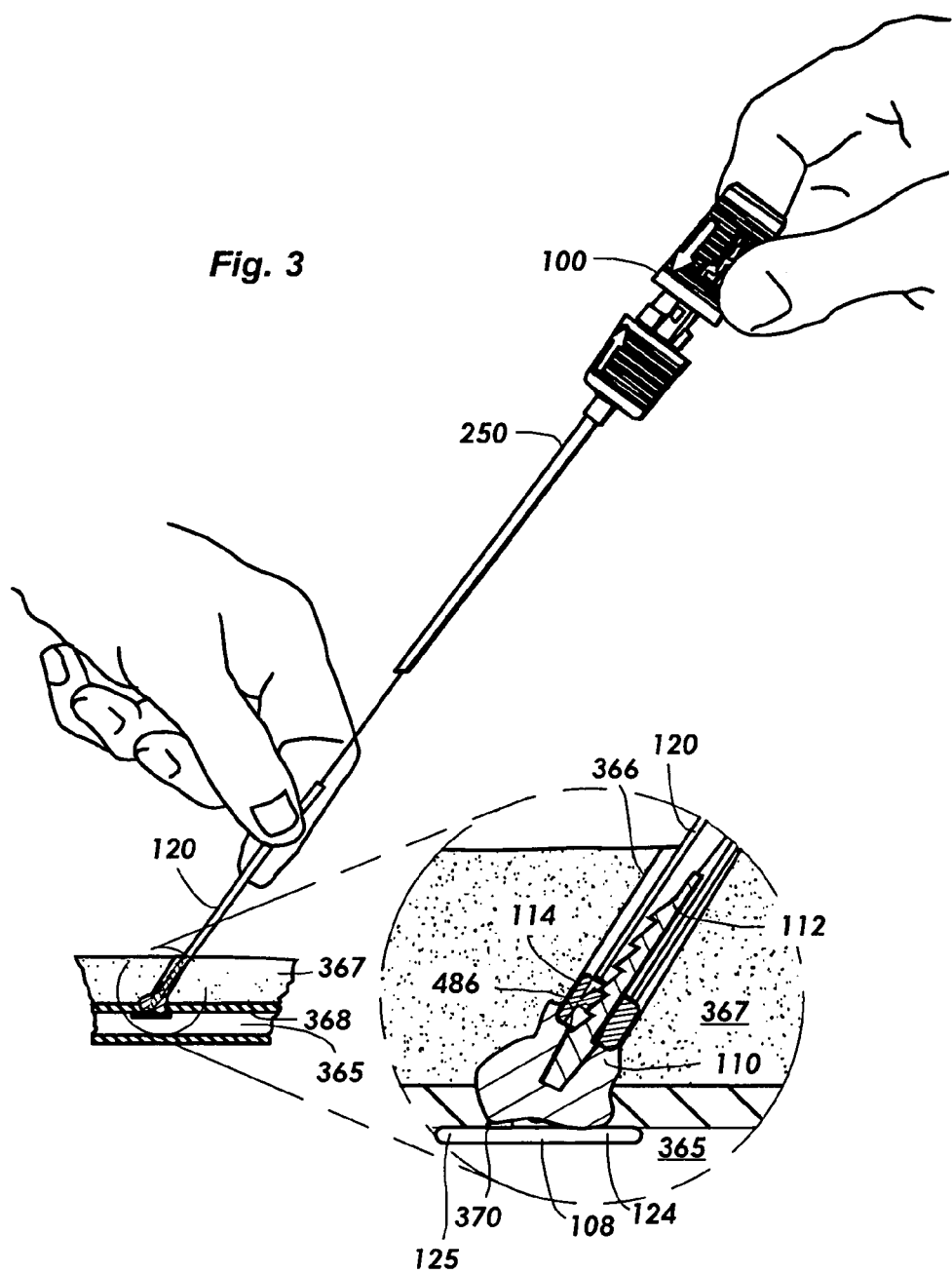
FIG. 3 is a perspective view of the tissue puncture closure device and insertion sheath of FIG. 2, showing an operator positioning a sealing plug with a locking apparatus according to one embodiment of the present invention.

However, depositing the collagen sponge 110 at the puncture 370 does not normally seal the puncture 370. Therefore, according to one embodiment of the present invention, an operator may apply a distal force to the tamping tube 120 as shown in FIG. 3. The tamping tube 120 advances the hub 114 distally along the strap 112 in response to the force on the tamping tube, and compresses the collagen sponge 110 toward the anchor 108, sandwiching and sealing the puncture 370 therebetween. Tension may be maintained on the suture 104 as the hub 114 is advanced by pulling on the suture 104 or the closure device 100. The geometry of the strap 112 and hub 114 creates a one-way locking apparatus that allows the hub 114 to advance distally along the strap 112 in a first direction, but prevents the hub 114 from retracting in a second or opposite direction. Therefore, the collagen sponge 110 slides along the strap 112, is compressed toward the anchor, and is held in position to seal the puncture 370 by the hub 114. Further, the strap 112 has a stop 486 that limits the travel of the hub 114, advantageously reducing the occurrence of over-tamping the collagen sponge 110, which can result in protrusion of the sponge into the artery 365.

Figure 4:
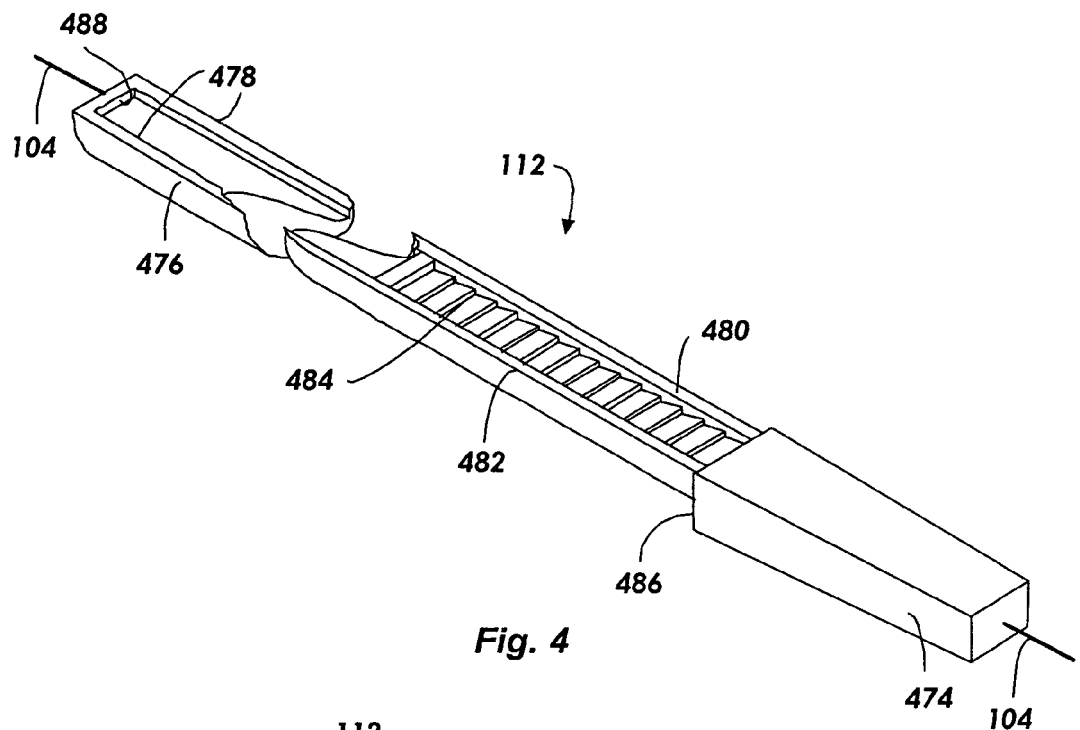
FIG. 4 is a perspective view of a strap of a locking apparatus according to one embodiment of the present invention.
Figure 5:
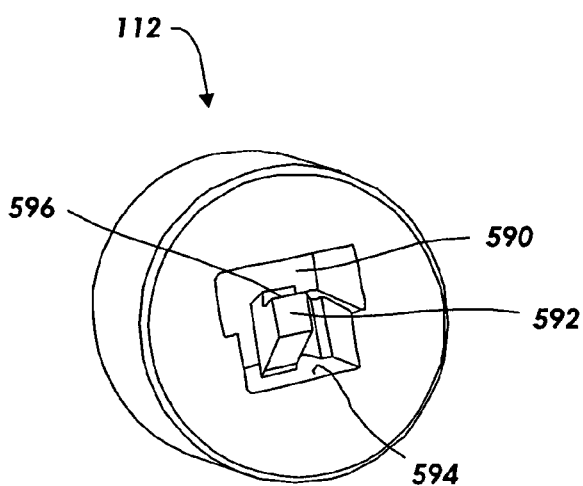
FIG. 5 is a perspective view of a hub of a locking apparatus according to one embodiment of the present invention.

The strap 112 and hub 114 are shown in more detail in FIGS. 4-5. The strap 112 and hub 114 comprise a one-way lock or ratchet such that the hub 114 can only move along the strap 112 in a first direction as mentioned above. Referring to FIG. 4, the strap 112 includes a biologically resorbable material and has a first end 474 and a second end 476. The strap 112 comprises an elongated track 478 that includes opposing walls 480, 482 extending at least partially along the longitudinal length of the of strap 112. The opposing walls 480, 482 are substantially parallel to one another according to the embodiment shown. Recessed between the opposing walls 480, 482 is a plurality of sloping teeth 484 that extend along a segment of the elongated track 478. However, the sloping teeth 484 may extend the entire length of the elongated track 478 according to some embodiments. The elongated track 478 ends with the shoulder stop 486 at the first end 474 of the strap 112. The strap 112 then tapers from the shoulder stop 486 to a tip of the first end 474. The second end 476 also includes a stop 488 to prevent the hub 114 (FIG. 5) from sliding off the second end 476.

Referring next to FIG. 5, the hub 114 is shown in perspective. The hub 114 is a generally cylindrical nut or disk and is also made of biologically resorbable materials. The hub 114 includes a generally T-shaped cavity 590 sized to accept the cross-section of the elongated track 478 (FIG. 4). The T-shaped cavity 590 is shaped to provide a snug, smooth fit over the elongated track 478 (FIG. 4) such that the hub 114 tends to remain in place without sliding along the elongated track 478 until acted upon by a deliberate force (e.g. from the tamping tube 120 per FIG. 3).

Figure 6:
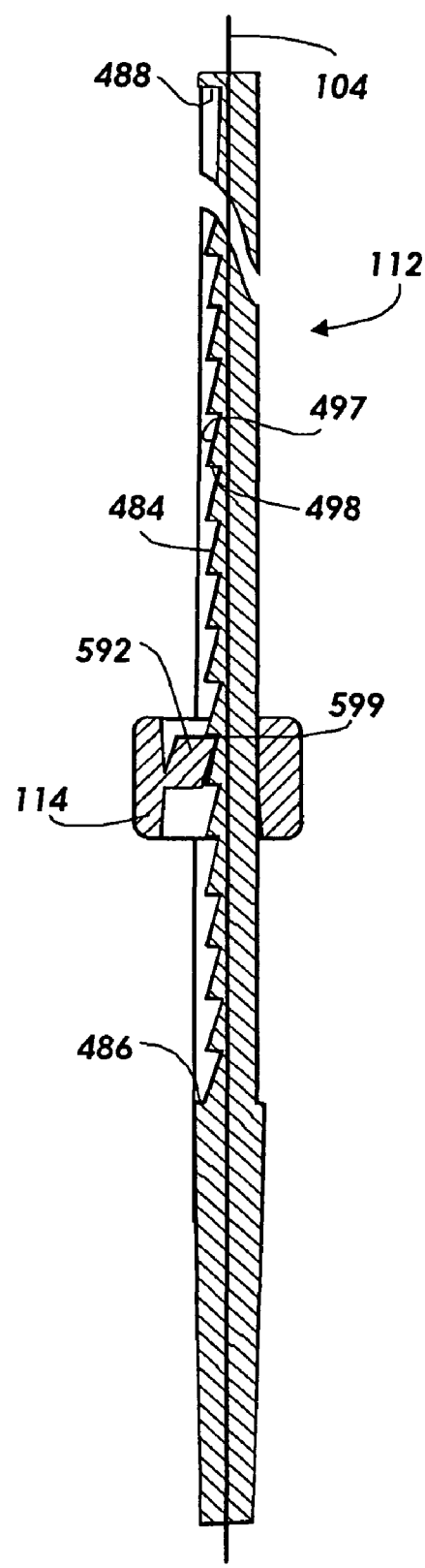
FIG. 6 is a cross-sectional view of the hub of FIG. 5 engaged with the strap of FIG. 4 according to one embodiment of the present invention.

Cantilevered from the T-shaped cavity 590 is a flexible internal finger 592. The flexible internal finger 592 extends from a first surface 594 at the bottom of the T-shaped cavity. The flexible internal finger 592 may include a step or notch 596 to engage one of the sloping teeth 484 of the strap 112. However, according to some embodiments there is no notch 596. The step or notch 596 may instead be replaced by an external corner 599 as shown in cross-section in FIG. 6. As shown in FIG. 6, a cross-section of the flexible internal finger 592 may thus be generally parallelogram-shaped.

Continuing to refer to FIG. 6, the hub 114 is shown engaged with the strap 112. The flexible internal finger 592 is flexible enough to displace laterally as the hub 114 is advanced distally (top to bottom as FIG. 6 is oriented). However, as the hub 114 is advanced along the strap 112 in degrees from tooth to tooth, the flexible finger 592 is biased to spring back and bear against a first surface 497 of the plurality of sloped teeth 484. Therefore, once one of the sloping teeth 484 is traversed, the hub 114 may not retract and return to any of the previously-traversed teeth 484. Instead, if the hub tends to retract proximally, the flexible internal finger 592 catches on a second surface 498 of the sloping teeth 484 and prevents movement in a second direction. The external corner 599 or the notch 596 (FIG. 5) may be shaped to mate with the second surface 498 of the sloped teeth 484 to further ensure that the hub 114 is locked from proximal movement along the strap 112. The hub 114 and strap 112 thus comprise one embodiment of the locking apparatus mentioned above used to compress and hold the collagen sponge 110 (FIG. 3) at the puncture 370 (FIG. 3). Other locking apparatus may also be integrated with the closure device 100 (FIG. 1) by those of skill in the art having the benefit of this disclosure.

Referring back to FIG. 3, the hub 114 may advance along the strap 112 only until the hub bears against the stop shoulder 486. Accordingly, the placement of the stop shoulder 486 and the size of the collagen sponge 110 may be chosen by one of skill in the art having the benefit of this disclosure such that when the hub 114 bears against the stop shoulder 486, the puncture 370 is optimally sealed between the collagen sponge 110 and the anchor 108 while also preventing the collagen sponge 110 from being over-tamped.

While the invention has been particularly shown and described with reference to embodiments thereof, it will be understood by those skilled in the art that various other changes in the form and details may be made without departing from the scope of the invention.

What is claimed is:

1. A tissue puncture closure device for partial insertion into and sealing of an internal tissue wall puncture, comprising:
   a filament;
   an anchor for insertion through the tissue wall puncture attached to the filament at a first end of the closure device;

a sealing plug disposed proximal of the anchor;
a locking apparatus separate from the filament, anchor, and sealing plug and arranged adjacent to the sealing plug for compressing the sealing plug along the filament toward the anchor, wherein the locking apparatus comprises a ratchet mechanism, the ratchet mechanism including a first member that maintains a fixed position relative to the filament and terminates proximal of a distal end of the filament, and a second member that is movable along the filament relative to and in contact with the first member and configured to apply a pressure to the sealing plug to form a seal between the tissue wall puncture and the sealing plug, wherein the pressure is insufficient to push the sealing plug through a portion of the internal tissue wall puncture.

2. A tissue puncture closure device for partial insertion into and sealing of an internal tissue wall puncture according to claim 1 wherein the locking apparatus comprises a strap and hub attached to the filament.

3. A tissue puncture closure device for partial insertion into and sealing of an internal tissue wall puncture according to claim 2 wherein the strap and hub comprise the ratchet mechanism.

4. A tissue puncture closure device for partial insertion into and sealing of an internal tissue wall puncture according to claim 3 wherein the strap comprises an elongated track and a plurality of sloping teeth.

5. A tissue puncture closure device for partial insertion into and sealing of an internal tissue wall puncture according to claim 3 wherein the strap comprises a shoulder stop limiting movement of the hub.

6. A tissue puncture closure device for partial insertion into and sealing of an internal tissue wall puncture according to claim 3 wherein the hub comprises a nut having a flexible internal finger biased to engage a plurality of sloping teeth.

7. A tissue puncture closure device for partial insertion into and sealing of an internal tissue wall puncture according to claim 6 wherein the flexible internal finger comprises a notch or an external corner shaped to mate a surface of the plurality of sloping teeth.

8. A tissue puncture closure device for partial insertion into and sealing of an internal tissue wall puncture according to claim 6 wherein the flexible internal finger of the hub freely traverses the sloping teeth in degrees in a first direction, but is prevented from traversing the sloping teeth in a second direction.

9. A tissue puncture closure device for partial insertion into and sealing of an internal tissue wall puncture according to claim 2, further comprising a tube slidingly disposed about the filament proximal to the hub for advancing the hub along the strap.

10. A tissue puncture closure device for partial insertion into and sealing of an internal tissue wall puncture according to claim 9 wherein the tube comprises an outer diameter that is larger than an inner diameter of the hub.

11. A tissue puncture closure device for partial insertion into and sealing of an internal tissue wall puncture according to claim 2 wherein the sealing plug is initially disposed over an outer diameter of the strap.

12. A tissue puncture sealing device comprising:
an internal component configured to be positioned against an internal wall of a lumen;
an external component configured to be positioned external to the lumen;
a filament attached to the internal component, the external component being slidable along the filament toward the internal component;
a locking apparatus that is separate from the internal and external components and the filament, the locking apparatus being configured to compress and hold the internal and external components together, wherein the locking apparatus comprises a ratchet mechanism, the ratchet mechanism including a first member that maintains a fixed position relative to the filament and the internal component, and a second member that is movable relative to and in contact with the external component and configured to apply a pressure to the external component to form a seal between the lumen and the external component, wherein the pressure is insufficient to push the external component through a portion of the lumen;
wherein the filament provides a pivotal connection of the internal component to the first member distally of the ratchet mechanism.

13. A tissue puncture sealing device according to claim 12 wherein the tissue puncture is an arteriotomy.

14. A tissue puncture sealing device according to claim 12 wherein the internal component is an anchor and the external component is a collagen sponge.

15. A tissue puncture sealing device according to claim 12 wherein the locking apparatus comprises a strap and hub.

16. A tissue puncture sealing device according to claim 15 wherein the strap and hub comprise the ratchet mechanism.

17. A tissue puncture sealing device according to claim 16 wherein the strap comprises an biologically resorbable elongated track and a plurality of sloping teeth.

18. A tissue puncture sealing device according to claim 17 wherein the hub comprises a nut having a flexible internal finger biased to engage the plurality of sloping teeth.

19. A tissue puncture sealing device according to claim 15, further comprising a tube slidingly disposed adjacent to the hub for pushing the hub along the strap.

20. A tissue puncture closure device for partial insertion into and sealing of a puncture in a vessel wall, comprising:
an carrier tube having first and second ends;
an anchor disposed outside of the carrier tube at the first end thereof;
a sealing plug disposed inside the carrier tube at the first end thereof;
a filament attached to the anchor and the sealing plug being slidable along the filament toward the anchor;
a one-way lock disposed at the first end of the carrier tube for compressing the sealing plug toward the anchor, the one-way lock being separate from the carrier tube, anchor, filament, and sealing plug, wherein the one-way lock comprises a ratchet mechanism, the ratchet mechanism including a first member that maintains a fixed position relative to the anchor, and a second member that is movable relative to and in contact with the first member to compress the sealing plug toward the anchor to seal the puncture without allowing the sealing plug to be forced into an interior region of the vessel;
wherein the filament provides a pivotal connection of the anchor to the first member distally of the ratchet mechanism.

21. A tissue puncture closure device for partial insertion into and sealing of an internal tissue wall puncture according to claim 20, further comprising a filament attaching the anchor to the one-way lock.

22. A tissue puncture closure device for partial insertion into and sealing of an internal tissue wall puncture according to claim 20 wherein the one-way lock is disposed within the first end of the carrier tube, and wherein the sealing plug is slidingly arranged about the one-way lock.

23. A tissue puncture closure device for partial insertion into and sealing of an internal tissue wall puncture according to claim 20 wherein the one-way lock comprises the ratchet mechanism.

24. A tissue puncture closure device for partial insertion into and sealing of an internal tissue wall puncture according to claim 20 wherein the ratchet mechanism comprises a strap and hub.

25. A tissue puncture closure device for partial insertion into and sealing of an internal tissue wall puncture according to claim 24 wherein the strap comprises a plurality of sloping teeth.

26. A tissue puncture closure device for partial insertion into and sealing of an internal tissue wall puncture according to claim 25 wherein the hub comprises a nut having a flexible internal finger biased to engage one or more of the plurality of sloping teeth.

27. A tissue puncture closure device for partial insertion into and sealing of an internal tissue wall puncture according to claim 20 wherein the anchor, sealing plug, and one-way lock comprise biologically resorbable materials.

28. A tissue puncture closure assembly for partial insertion into and sealing of an internal tissue wall puncture, comprising:
an insertion sheath receptive of a closure device;
the closure device, comprising:
a carrier tube;
a filament extending at least partially through the carrier tube;
an anchor for insertion through the internal tissue wall puncture attached to the filament at a first end of the closure device;
a strap and locking hub attached to the filament adjacent to the anchor, the hub being movable along and in contact with the strap in a first direction, but locked from moving opposite of the first direction;
a sealing plug disposed at least partially about the strap and adjacent to the locking hub, wherein the strap and hub comprise a ratchet mechanism configured to apply a pressure to the sealing plug to compress the sealing plug along the strap toward the anchor to form a seal between the tissue wall puncture and the sealing plug, wherein the pressure is insufficient to push the sealing plug through a portion of the internal tissue wall puncture;
wherein the strap and locking hub are separate from the filament, anchor and sealing plug and are positioned proximal of the anchor and a distal end of the filament.

29. A tissue puncture closure assembly for partial insertion into and sealing of an internal tissue wall puncture according to claim 28 wherein the insertion sheath further comprises a one-way valve at a first end and a hemostatic valve at a second end.

30. A tissue puncture closure assembly for partial insertion into and sealing of an internal tissue wall puncture according to claim 28 wherein the closure device further comprises a tube slidingly disposed about the filament adjacent to the locking hub for pushing the hub along the strap in the first direction.

31. A tissue puncture closure device for partial insertion into and sealing of an internal tissue wall puncture according to claim 1 wherein the anchor is pivotally attached to the filament.

32. A tissue puncture closure device for partial insertion into and sealing of an internal tissue wall puncture according to claim 1 wherein the filament comprises a single strand extending through the sealing plug and attached at a distal end to the anchor.

33. A tissue puncture closure device for partial insertion into and sealing of an internal tissue wall puncture according to claim 1 wherein the first member is molded around the filament.

34. A tissue puncture closure device for partial insertion into and sealing of an internal tissue wall puncture according to claim 1 wherein the first member is connected to the filament at a location spaced between distal and proximal ends of the filament.

* * * * *